United States Patent [19]

Finkelstein et al.

[11] Patent Number: 4,835,154

[45] Date of Patent: May 30, 1989

[54] 1-ARALYKYL-5-PIPERAZINYLMETHYL-2-MERCAPTOIMIDAZOLES AND 2-ALKYLTHIOIMIDAZOLES AND THEIR USE AS DOPAMINE-β-HYDROXYLASE INHIBITORS

[75] Inventors: Joseph A. Finkelstein, Philadelphia, Pa.; Lawrence I. Kruse, Tewin, England

[73] Assignee: SmithKline Beckman Corporation, Philadelphia, Pa.

[21] Appl. No.: 56,018

[22] Filed: Jun. 1, 1987

[51] Int. Cl.$^4$ .................... A61K 31/495; C07D 403/06
[52] U.S. Cl. ........................................ 514/252; 544/370
[58] Field of Search ........................... 544/370; 514/252

[56] References Cited

U.S. PATENT DOCUMENTS

| 3,505,334 | 4/1970 | Regnier et al. | 544/392 |
| 4,022,783 | 5/1977 | Shroff et al. | 544/370 |
| 4,338,453 | 7/1982 | Gall | 548/263 |
| 4,487,761 | 12/1984 | Cole et al. | 546/296 |
| 4,532,331 | 6/1985 | Frazee et al. | 548/342 |
| 4,603,130 | 7/1986 | Iemura et al. | 544/370 |

FOREIGN PATENT DOCUMENTS 125033 11/1984 European Pat. Off. .
2022073 12/1979 United Kingdom ................ 544/370
2091255 7/1982 United Kingdom ................ 544/370

Primary Examiner—Donald G. Daus
Assistant Examiner—Cecilia Shen
Attorney, Agent, or Firm—Mary E. McCarthy; Stuart R. Suter; Alan D. Lourie

[57] ABSTRACT

Potent dopamine-β-hydroxylase inhibitors having the Formula

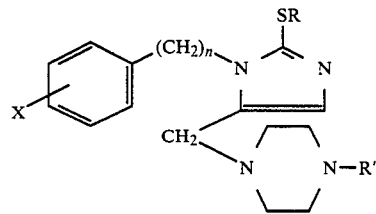

that are useful to inhibit dopamine-β-hydroxylase activity, pharmaceutical compositions including these inhibitors, and methods of using these inhibitors to inhibit dopamine-β-hydroxylase activity in mammals. Also disclosed are novel intermediates useful in preparing the presently invented inhibitors.

9 Claims, No Drawings

1-ARALYKYL-5-PIPERAZINYLMETHYL-2-MERCAPTOIMIDAZOLES AND 2-ALKYLTHIOIMIDAZOLES AND THEIR USE AS DOPAMINE-βHYDROXYLASE INHIBITORS

FIELD OF THE INVENTION

This invention relates to novel compounds that inhibit dopamine-β-hydroxylase.

BACKGROUND OF THE INVENTION

In the catecholamine biosynthetic pathway, tyrosine is converted in three steps to norepinephrine (NE). Intermediates are dihydroxyphenylalanine (DOPA) and dopamine (DA). Dopamine is hydroxylated to norepinephrine by dopamine-β-hydroxylase (DBH) in the presence of oxygen and ascorbic acid.

Inhibition of catecholamine activity decreases blood pressure. Weinshilboum, *Mayo Clin. Proc.* 55, 39 (1980), reviews compounds that inhibit catecholamine activity by acting upon adrenergic receptors. Alternatively, the catecholamine biosynthetic pathway can be suppressed at any of the three steps, resulting in reduced NE levels. In addition to producing an antihypertensive effect, inhibitors of NE synthesis are active as diuretics, natriuretics, cardiotonics, and vasodilators. Inhibition of DBH activity can have the added advantage of increasing DA levels, which as reported by Ehrreich et al., "New Antihypertensive Drugs," Spectrum Publishing, 1976, pp. 409-432, has selective vasodilator activity at certain concentrations.

DBH inhibitors also have been shown to reduce or prevent formation of gastric ulcers in rats by Hidaka et al., "Catecholamine and Stress," edit. by Usdin et al., Permagon Press, Oxford, 1976, pp. 159-165 and by Osumi et al., *Japan J. Pharmacol.* 23, 904 (1973).

A number of DBH inhibitors are known. These generally are divided into two classes, namely, metal chelating agents, which bind copper in the enzyme, and phenethylamine analogues. Rosenberg et al., "Essays in Neurochemistry and Neuropharmacology," Vol. 4, ed. by Youdim et al., John Wiley & Sons, 1980, pp. 179-192, and Goldstein, *Pharmacol. Rev.* 18(1), 77 (1966), review DBH inhibitors. The former report that many potent DBH inhibitors have a hydrophobic side chain of size comparable to the aromatic ring of DA, leading the authors to suggest that incorporation of a terminal hydroxyl group on a 4- to 6-carbon side chain on a phenethylamine analogue may yield potent inhibitors.

Known DBH inhibitors include:

(a) 5-alkylpicolinic acids [See, Suda et al., *Chem. Pharm. Bull.* 17, 2377 (1969); Umezawa et al., *Biochem. Pharmacol.* 19, 35 (1969); Hidaka et al., *Mol. Pharmacol.* 9, 172 (1973); Miyano e al., *Chem. Pharm. Bull.* 26, 2328 (1978); Miyano et al., *Heterocycles* 14, 755 (1980); Claxton et al., *Eur. J. Pharmacol.* 37, 179 (1976)];

(b) BRL 8242 [See Claxton et al; Eur J. Pharmacol. 37, 179 (1976)];

(c) 1-alkylimidazole-2-thiols [See, Hanlon et al., *Life Sci.* 12, 417 (1973); Fuller et al., *Adv. Enzyme Regul.* 15, 267 (1976)];

(d) substituted thioureas [See, Johnson et al., *J. Pharmacol. Exp. Ther.* 168, 229 (1969) ]; and (e) benzyloxyamine and benzylhydrazine [See, Creveling et al., *Biochim. Biophys. Acta* 64, 125 (1962); Creveling et al., *Biochim. Biophys. Acta* 8, 215 (1962); Van Der Schoot et al., *J. Pharmacol. Exp. Ther.* 141, 74 (1963); Bloom, *Ann. N.Y. Acad. Sci.* 107, 878 (1963)].

All the above compounds except benzyloxamine and benzylhydrazine apparently owe their inhibitory effect to metal chelating properties. Alkyl derivatives of imidazole-2-thiol are more potent, presumably due to non-specific interaction of the alkyl substituent with the enzyme. Benzyloxyamine and benzylhydrazine are phenethylamine analogues which apparently act as competitive inhibitors.

In addition to the above compounds, Runti et al., *Il Farmaco Ed. Sci.* 36, 260 (1980), report that other fusaric acid derivatives and analogues inhibit DBH. These include phenylpicolinic acid, which has twice the inhibitory activity of fusaric acid, and 5-(4-chlorobutyl) picolinic acid, and others such as substituted amides of fusaric acid and acids and amides of 5-butyroylpicolinic acid, 5-aminopicolinic acid and 5-hydrazinopicolinic acid, and derivatives thereof.

Hidaka et al., *Molecular Pharmacology*, 9, 172-177 (1972) report that 5-(3,4-dibromobutyl)picolinic acid and 5-(dimethyldithiocarbamoylmethyl)picolinic acid are DBH inhibitors.

Bupicomide, 5-(n-butyl)picolinamine, is reported by Ehrreich et al., "New Antihypertensive Drugs", Spectrum Publications, 1976, pg, 409-432, to be a DBH inhibitor that has antihypertensive activity.

In European Patent Application No. 125,033 (published Nov. 14, 1984) a series of 1-phenyl and 1-phenylalkylimidazole compounds having a mercapto or alkylthio group in the 2-position are disclosed. These compounds are described as having DBH inhibiting activity.

U.S. Pat. No. 4,487,761 describes several methylpyridine derivatives isolated from the fermentation broth of a strain of Streptoverticillium. These compounds inhibit DBH activity.

U.S. Pat. No. 4,532,331 describes various 1-benzyl-2-aminomethylimidazole derivatives that inhibit DBH activity and includes pharmaceutical compositions containing these derivatives and methods of using these derivatives to inhibit DBH activity.

Non-specific, often toxic effects to known DBH inhibitors have obviated clinical use of these compounds. Fusaric acid, for example, is hepatotoxic. See, for example, Teresawa et al., *Japan. Cir. J.* 35, 339 (1971) and references cited therein. Presumably, the picolinic acid structures interacts with a number of metalloproteins and enzymes non-specifically to produce the observed side effects.

SUMMARY OF THE INVENTION

The present invention resides in the discovery that DBH is inhibited by substituted 1-aralkyl-5-piperazinylmethyl-2-mercaptoimidazole and 2-alkylthioimidazole compounds. These compounds are potent and produce prolonged DBH inhibition.

Presently preferred compounds of the invention and compounds included in the pharmaceutical compositions and used in the methods of the invention include:

1-(3,5-difluorobenzyl)-5-[(4-methyl-1-piperazinyl)methyl]-2-mercaptoimidazole.

In a further aspect of the invention there are provided novel intermediates useful in preparing substituted 1-aralkyl-5-piperazinylmethyl-2-mercaptoimidazole and 2-alkylthioimidazole compounds.

The invention also is a method of inhibiting DBH activity in mammals, including humans, which comprises administering internally to a subject an effective amount of a substituted 1-aralkyl-5-piperazinylmethyl-2-mercaptoimidazole and 2-alkylthioimidazole compounds.

Included in the present invention are pharmaceutical compositions comprising compounds useful in the method of the invention and a pharmaceutical carrier.

DETAILED DESCRIPTION OF THE INVENTION

The presently invented compounds that inhibit DBH have the following formula:

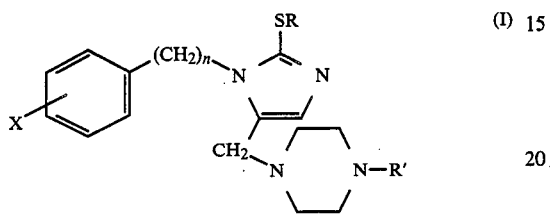

in which:

X is H, F, Cl, Br, I, $C_{1-4}$alkyl, CN, $NO_2$, $SO_2NH_2$, COOH, OH, CHO, $C_{1-4}$alkoxy, $CH_2OH$, $CH_2OC_{1-4}$alkyl, $CF_3$, $C_2F_5$, $C_3F_7$, $SO_2CH_3$, $SO_2CF_3$, or $CO_2C_aH_{2a+1}$ wherein a is 1–5, or any accessible combination thereof of up to 5 substituents;

n is 1–5; and

R and R' independently are hydrogen or $C_{1-4}$-alkyl; or any pharmaceutically acceptable salt or hydrate thereof.

As used herein, "accessible combination thereof" means any combination of the substituents that is available by chemical synthesis and is stable.

It is intended that Formula I includes the tautomer of the compounds in which R is hydrogen, that is, compounds having the above formula wherein the imidazole moiety has either of the below formulae:

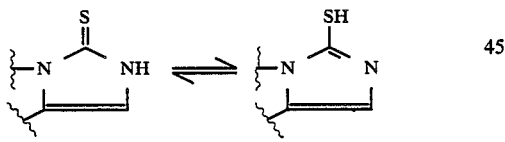

The Formula I compounds are prepared from corresponding cyanobenzenes and cyanoalkylbenzenes by processes such as shown in Scheme I, below. The starting cyanobenzenes and cyanoalkylbenzenes are known and described in published references or can be obtained readily.

SCHEME I

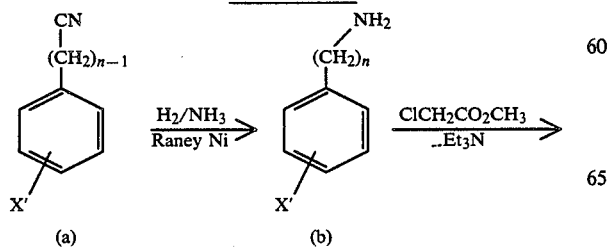

-continued
SCHEME I

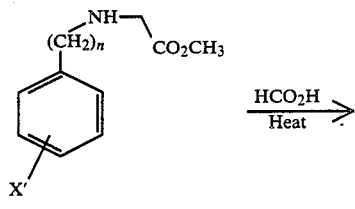

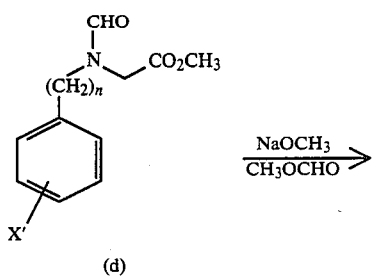

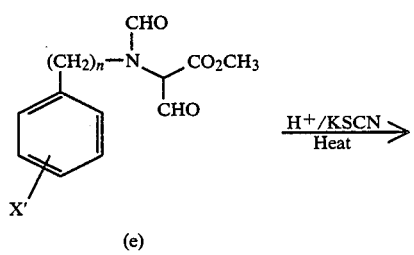

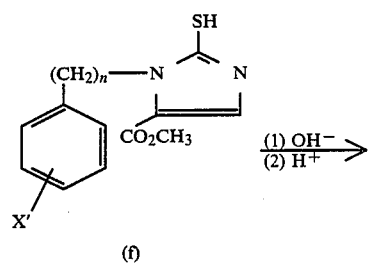

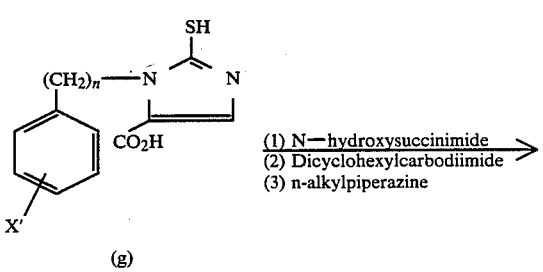

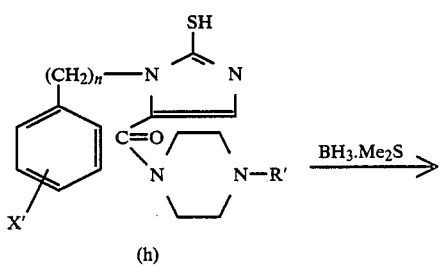

-continued
SCHEME I

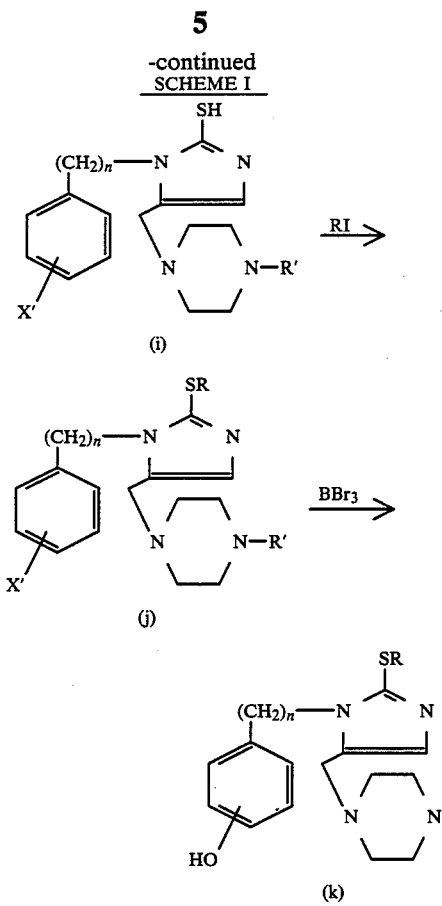

In Scheme I, n, R', and R are as defined in Formula I, and X' is X except OH. Scheme I illustrates hydrogenation of starting cyanoalkylbenzenes (a) using a suitable hydrogenation catalyst, preferably Raney nickel in methanol, which is added to a formula (a) compound in a suitable organic solvent, such as a $C_{1-4}$alkyl alcohol, preferably methanol, saturated with ammonia. The formula (b) amines thus prepared then are reacted with a $C_{1-4}$alkylhalo acetate, preferably methyl chloroacetate in presence of an organic base, preferably triethylamine, to yield formula (c) compounds.

Next, the formula (c) compounds in a suitable organic solvent, preferably xylene, are reacted with formic acid to produce formula (d) compounds. Formula (e) compounds are prepared by adding a formula (d) compound in a $C_{1-4}$alkyl formate, preferably methyl formate, to a suitable organic base, preferably sodium methoxide. Then formula (e) compounds in a suitable solvent such as water:methanol (1:1) are heated with a strong acid, preferably hydrochloric acid, and a thiocyanate salt, preferably potassium thiocyanate to yield formula (f) compounds. Ester hydrolysis of formula (f) compounds with strong base, preferably sodium hydroxide, followed by treatment with strong acid, preferably hydrochloric acid, yields formula (g) free acids.

Thereafter, to a formula (g) compound in a suitable organic solvent, preferably tetrahydrofuran, is added a coupling agent such as N-hydroxyphthalimide, N-hydroxybenzotriazole, or, preferably N-hydroxysuccinimide, followed by addition of an activating agent such as ethylchloroformate, 1-ethoxycarbonyl-2-ethoxy-1,2-dihydroquinoline, trifluoroacetic anhydride, or, preferably dicyclohexylcarbodiimide. Then, a N-R'-piperazine in a suitable organic solvent, preferably tetrahydrofuran, is added to produce a formula (h) compound. Formula (i) compounds, which are Formula (I) compounds wherein R is hydrogen, are prepared by treating formula (h) compounds with a suitable reducing agent, preferably, borane and methylsulfide.

When desired, formula (k) compounds are prepared from formula (j) compounds wherein X' is $C_{1-4}$alkoxy using known hyrolysis methods, for example by treatment with boron tribromide, or hydrogen bromide in an appropriate solvent.

Optionally, formula (j) compounds, Formula (I) compounds in which R is $C_{1-4}$alkyl, are prepared by alkylating formula (i) compounds using an appropriate R-halide such as methyl iodide or butylbromide in a $C_{1-4}$alkyl alcohol such as methanol.

In preparing the presently invented compounds of Formula (I), novel intermediate compounds of the following formula were synthesized:

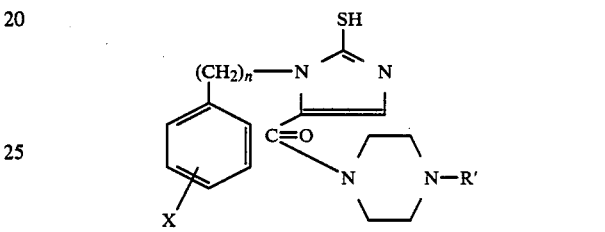

in which:

X is H, F, Cl, Br, I, $C_{1-4}$alkyl, CN, $NO_2$, $SO_2NH_2$, COOH, OH, CHO, $C_{1-4}$alkoxy, $CH_2OH$, $CH_2OC_{1-4}$alkyl, $CF_3$, $C_2F_5$, $C_3F_7$, $SO_2CH_3$, $SO_2CF_3$, or $CO_2C_aH_{2a+1}$ wherein a is 1-5, or any accessible combination thereof of up to 5 substituents;

n is 1-5; and

R' is hydrogen or $C_{1-4}$alkyl.

The pharmaceutically acceptable acid addition salts of compounds of the invention are formed with appropriate strong or moderately strong organic or inorganic acids by methods known in the art. For example, the base is reacted with a suitable inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Exemplary of the salts which are included in this invention are maleate, fumarate, lactate, oxalate, methanesulfonate, ethanesulfonate, benzenesulfonate, tartrate, citrate, hydrochloride, hydrobromide, sulfate, phosphate, quinate, and nitrate salts.

Because the Formula I compounds inhibit DBH activity, they have therapeutic value as diuretic, natriuretic, cardiotonic, antihypertensive, and vasodilator agents, as well as antiulcerogenic and anti-Parkinsonian agents. Listed in Table I is the compound of the invention that was tested for in vitro DBH inhibition by a standard procedure for assaying conversion of tyramine to octopamine in the presence of DBH. J. J. Pisano, et al., Biochim. Biophys. Acta, 43, 566–568 (1960). Octopamine was assayed following sodium periodate oxidation to p-hydroxybenzaldehyde by measuring spectrophotometric absorbance at 330 nm. In Table I, inhibition is given in molar concentration of compound at which DBH activity was halved ($IC_{50}$). Fusaric acid, by this test has an $IC_{50}$ of $8 \times 10^{-7}$M.

TABLE I

| Compound | DBH IC$_{50}$ |
|---|---|
| 1-(3,5-Difluorobenzyl)-5-[(4-methyl-1-piperazinyl)methyl]-2-mercaptoimidazole | $5.9 \times 10^{-4}$ M |

Further, spontaneously hypertensive rats were treated with the compound in Table I at a dose of 50 mg/kg intraperitoneally, and mean arterial blood pressure was monitored for 260 minutes using indwelling cannulae in the tail arteries. When compound to vehicle-treated controls, the animals treated with the invented compound exhibited significant blood pressure reductions within 30 minutes following treatment. The maximal blood pressure reduction was approximately 25 mmHg.

The Formula I compounds are incorporated into convenient pharmaceutical dosage forms such as capsules, tablets, or injectable preparations. Solid or liquid pharmaceutical carriers can be employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid, or an aqueous or nonaqueous liquid suspension.

The pharmaceutical preparations are made following conventional techniques of a pharmaceutical chemist involving mixing, granulating and compressing, when necessary, for tablet forms, or mixing, filling, and dissolving the ingredients, as appropriate, to give the desired oral or parenteral products.

Doses of the present compounds of Formula (I) in a pharmaceutical dosage unit as described above will be an efficacious, nontoxic quantity selected from the range of 0.1–100 mg/kg of active compound, preferably 0.1–50 mg/kg. The selected dose is administered to a human patient in need of DBH inhibition from 1–6 times daily, orally, rectally, by injection, or continuously by infusion. Oral dosage units for human administration preferably contain from 1 to 500 mg of active compound. Parenteral administration, which uses lower dosages is preferred. Oral administration, at higher dosages, however, also can be used when safe and convenient for the patient.

The method of this invention of inhibiting DBH activity in mammals, including humans, comprises administering internally to a subject in need of such inhibition an effective DBH inhibiting amount of a Formula (I) compound.

The following examples are illustrative of preparation of Formula (I) compounds. The examples are not intended to limit the scope of the invention as defined hereinabove and as claimed below.

EXAMPLE 1

1-(3,5-Difluorobenzyl)-5-[(4-methyl-1-piperazinyl)methyl]-2-mercaptoimidazole (i) 3,5-Difluorobenzylamine A slurry of Raney nickel in methanol was added to a solution of 3,5-difluorobenzonitrile (12.0 g., 0863 mole) in methanol (100 ml) saturated with ammonia and the mixture was hydrogenated for 2.5 hours at 50 pounds pressure. The solution was decanted from the catalyst and the catalyst washed four times with methanol and decanted. The combined decanted solvent was evaporated and the residue dissolved in ethyl acetate and extracted twice with 1N hydrochloric acid (50 ml). The acid solution was made basic with 10% sodium hydroxide and extracted with three portions of ethyl acetate. The ethyl acetate was washed with water, brine, dried over sodium sulfate and the solvent removed to give the product as an oil (12.3 g, 100%).

(ii) N-(3,5-Difluorobenzyl)glycine methyl ester

A solution of 3,5-difluorobenzylamine (12.3 g, 0.0863 mole), methyl chloroacetate (7.6 ml, 0.0863 mole) and triethylamine (12.0 ml, 0.0863 mole) in dry dimethylformamide (85 ml) was heated at 60° C. for 3 hours. The mixture was diluted with an equal volume of ether and the triethylamine hydrochloride filtered. The filtrate was concentrated under vacuum and the resultant oil triturated with ethyl acetate and the solution decanted from a small amount of residual oil. The solvent was removed and the product was purified by flash chromatography (silica) by eluting with hexane-ethyl acetate (70:30) to give an oil (7.61 g, 41%).

(iii) N-Formyl-N-(3,5-difluorobenzyl)glycine methyl ester

A solution of N-(3,5-difluorobenzyl)-glycine methyl ester (7.61 g, 0.0352 mole) and formic acid (1.33 ml, 0.0352 mole) was heated at reflux in xylene (60 ml) with azeotroic removal of water for 2.5 hours and the solvent was removed under vacuum to give the product as an oil (8.50 g, 99%).

(iv) 1-(3,5-Difluorobenzyl)-2-mercaptoimidazole-5-carboxylic acid methyl ester

Methanol (1.54 ml, 0.0381 mole) was added to a suspension of sodium (0.876 g, 0.0381 mole) in dry tetrahydrofuran and the mixture stirred for 30 minutes. A solution of N-formyl-N-(3,5-difluorobenzyl)-glycine methyl ester (8.50 g, 0.0349 mole) in methyl formate (6.57 ml, 0.107 mole) was added dropwise with cooling at 10° to 15° C. and the resulting mixture was stirred overnight at room temperature. The solvent was removed under vacuum and the residue was diluted with 100 ml water-methanol (1:1). The solution was treated with activated carbon, filtered, and cooled in ice. Hydrochloric acid (12N, 6.4 ml) and a solution of potassium thiocyanate (4.25 g, 0.0437 mole) in a minimum amount of water were added and the resulting solution was heated at 65°–70° C. for 24 hours. The solution was treated with activated carbon, filtered and the solvent was removed under vacuum until a precipitate formed. The mixture was cooled in ice and the product filtered and washed with a mixture of methanol-water. The product was trituarted with ethanol, filtered and dried to give a solid melting at 177°–178° C. (6.75 g, 68%).

(v) 1-(3,5-Difluorobenzyl)-2-mercaptoimidazole-5-carboxylic acid

A solution of sodium hydroxide (2.70 g, 0.0674 mole) in water (110 ml) was added to 1-(3,5-difluorobenzyl)-2-mercaptoimidazole-5-carboxylic acid methyl ester (6.39 g, 0.0225 mole) and the resulting solution was stirred for 2 hours. The solution was cooled in ice, acidified to pH 2 with 3N hydrochloric acid and the product was filtered and dried. The product was recrystallized from ethanol-water and dried to give a solid melting at 240°–241° C. (5.66 g, 93%).

(vi) 1-(3,5-Difluorobenzyl)-5-[(4-methyl-1-piperazinyl)carbonyl]-2-mercaptoimidazole To a solution of 1-(3,5-difluorobenzyl)-2-mercaptoimidazole-5-carboxylic acid (2.70 g, 0.01 moles) in tetrahydrofuran (25 ml) was added N-hydroxysuccinimide (1.27 g, 0.011 mole) followed by dropwise addition of dicyclohexylcarbodiimide (2.06 g, 0.01 mole) in tetrahydrofuran (30 ml). A solution of N-methylpiperazine (1.22 ml, 0.011 mole) in tetrahydrofuran (10 ml) was added and the mixture stirred at 25° C. for 2 hours and then at 40° C. for 16 hours. Additional N-methylpiperazine (1.0 ml, 0.009 mole) was added and the reaction mixture was stirred at 40° C. for 1.5 hours. The reaction mixture was filtered and the solvent removed under vacuum. The residue was dissolved in ethyl acetate and was washed with dilute sodium carbonate, water, and brine. The solution was dried and the solvent removed under vacuum. The resulting solid was triturated with ether and the product was filtered and dried to give a solid, m.p.: 243°–244° C. (2.10 g, 60%).

(vii) 1-(3,5-Difluorobenzyl)-5-[(4-methyl-1-piperazinyl)methyl]-2-mercaptoimidazole To a solution of 1-(3,5-difluorobenzyl)-5-[(4-methyl-1-piperazinyl)carbonyl]-2-mercaptoimidazole (1.37 g, 3.89 mmole) in chloroform (15 ml) was added dropwise 1 molar borane-methyl sulfide (23.3 ml, 23.3 mmole) and the solution was stirred for 4 hours at 25° C. The reaction mixture was cooled in ice and methyl alcohol was added dropwise until gas evolution ceased. The solvent was removed by evaporation at reduced pressure, ten portions of methyl alcohol were added, the reaction mixture was heated at reflux for 5 minutes and the solvent was removed at reduced pressure. The crude product was dissolved in methylene chloride-methanol (9:1) and purified by flash silica chromatography. The product was purified by trituration with ethyl acetate and recrystallization from ethanol to give 1-(3,5-difluorobenzyl)-5-[(4-methyl-1-piperazinyl)methyl]-2-mercaptoimidazole as a solid, m.p.: 200°–201° C. (0.820 g, 62%).

EXAMPLE 2

1-(3,5-Difluorobenzyl)-5-[(4-methyl-1-piperazinyl)methyl]imidazole-2-methylthioimidazole Reaction of 1-(3,5-difluorobenzyl)-5-[(4-methyl-1-piperazinyl)methyl]imidazole-2-thiol prepared as in Example 1 with methyl iodide and sodium methoxide in methanol by known techniques yields 1-(3,5-difluorobenzyl)-5-[(4-methyl-1-piperazinyl)methyl]imidazole-2-methylthioimidazole.

EXAMPLE 3

1-(3-Phenylpropyl)-5-[(4-methyl-1-piperazinyl)methyl]-2-mercaptoimidazole

The Example 1 process wherein 3-phenylpropionitrile replaces 3,5-difluorobenzylnitrile yields 1-(3-phenylpropyl)-5-[(4-methyl-1-piperazinyl)methyl]-2-mercaptoimidazole.

EXAMPLE 4

1-(2-Methoxybenzyl)-5-[(4-methyl-1-piperazinyl)methyl]-2-mercaptoimidazole

The Example 1 process wherein 3,5-difluorobenzonitrile is replaced by 2-methoxybenzonitrile yields 1-(2-methoxybenzyl)-5-[(4-methyl)-1-piperazinylmthyl]-2-mercaptoimidazole.

EXAMPLE 5

1-(2-Hydroxybenzyl)-5-[(4-methyl-1-piperazinyl)methyl]-2-mercaptoimidazole

Treatment of 1-(2-methoxybenzyl)-5-[4-methyl-1-piperazinyl)methyl]-2-mercaptoimidazole, prepared as in Example 4, in methylene chloride with boron tribromide yields 1-(2-hydroxybenzyl)-5-[4-methyl-1-piperazinyl)methyl]-2-mercaptoimidazole.

EXAMPLE 6

1-(3,5-Difluorobenzyl)-5-[(4-propyl-1-piperazinyl)methyl]-2-mercaptoimidazole

The Example 1 process wherein N-methylpiperazine is replaced by N-propylpiperazine yields 1-(3,5-difluorobenzyl)-5-[(4-propyl-1-piperazinyl)methyl]-2-mercaptoimidazole.

EXAMPLE 7

1-(3-Nitrobenzyl)-5-[(4-methyl-1-piperazinyl)methyl]-2-mercaptoimidazole

The Example 1 process wherein the 3,5-difluorobenzylamine intermediate is replaced by 3-nitrobenzylamine yields 1-(3-nitrobenzyl)-5-[(4-methyl-1-piperazinyl)methyl]-2-mercaptoimidazole.

EXAMPLE 8

1-(3,5-Difluoro-4-ethoxybenzyl)-5-[(4-methyl-1-piperazinyl)methyl]-2-mercaptoimidazole The process of Example 1 wherein 3,5-difluorobenzolnitrile is replaced by 3,5-difluorobenzyl-4-ethoxybenzonitrile yields 1-(3,5-difluoro-4-methoxybenzyl)-5-[(4-methyl-1-piperazinyl)methyl]-2-mercaptoimidazole.

EXAMPLE 9

1-(3,5-Dichloro-2-methyl-4-acetoxybenzyl)-5-[(4-methyl-1-piperazinyl)methyl]-2-mercaptoimidazole The Example 1 process wherein 3,5-difluorobenzonitrile is replaced by 3,5-dichloro-2-methyl-4-acetoxybenzonitrile yields 1-(3,5-dichloro-2-methyl-4-acetoxybenzyl)-5-[(4-methyl-1-piperazinyl)methyl]-2-mercaptoimidazole.

EXAMPLE 10

1-(3-Trifluoromethyl-5-hydroxymethylbenzyl)-5-[(4-methyl-1-piperazinyl)methyl]-2-mercaptoimidazole The Example 1 process wherein 3,5-difluorobenzonitrile is replaced by 3-trifluoromethyl-5-hydroxymethylbenzonitrile yields 1-(3-trifluoromethyl-5-hydroxymethyl)-5-[(4-methyl-1-piperazinyl)methyl]-2-mercaptoimidazole.

EXAMPLE 11

An oral dosage form for administering the presently invented compounds is produced by screening, mixing, and filling into hard gelatin capsules the ingredients in the proportions shown in Table II, below.

TABLE II

| Ingredients | Amounts |
| --- | --- |
| 1-(3,5-Difluorobenzyl)-5-[(4-methyl-1-piperazinyl)methyl]-2-mercaptoimidazole | 50 mg |
| magnesium stearate | 5 mg |

TABLE II-continued

| Ingredients | Amounts |
| --- | --- |
| lactose | 75 mg |

EXAMPLE 12

The sucrose, calcium sulfate dihydrate, and Formula (I) compound shown in Table III below, are mixed and granulated in the proportions shown with a 10% gelatin solution. The wet granules are screened, dried, mixed with the starch, talc and stearic acid, screened and compressed into a tablet.

TABLE III

| Ingredients | Amounts |
| --- | --- |
| 1-(3,5-Difluorobenzyl)-5-[4-methyl-1-piperazinyl)methyl]-2-mercaptoimidazole | 100 mg |
| calcium sulfate dihydrate | 150 mg |
| sucrose | 20 mg |
| starch | 10 mg |
| talc | 5 mg |
| stearic acid | 3 mg |

EXAMPLE 13

1-(3,5-Difluorobenzyl)-5-[(4-methyl-1-piperazinyl)-methyl]-2-mercaptoimidazole hydrochloride, 75 mg, is dispursed in 25 ml of normal saline to prepare an injectable preparation.

Contemplated equivalents of Formula (I) compounds are compounds that upon administration to mammals, including humans, are metabolized to Formula (I) compounds or metabolized to any Formula (I) compound active metabolites in sufficient amounts to produce the physiologic activity of Formula (I) compounds. Such compounds also would be included in the invented pharmaceutical compositions and used in the invented methods.

While the preferred embodiments of the invention are illustrated by the above, it is to be understood that the invention is not limited to the precise instructions herein disclosed and that the right to all modifications coming within the scope of the following claims is reserved.

What is claimed is:

1. A compound represented by the formula:

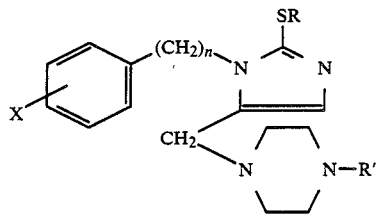

in which: hydrogen, 3,5-difluoro, 2-methoxy, 2-hydroxy, 3-nitro, 3,5-difluoro-4-ethoxy, 3,5-dichloro-2-methyl-4-acetoxy, or 3-trifluoromethyl-5-hydroxymethyl;

R and R' independently are H or $C_{1-4}$alkyl; and n is 1–5; or any pharmaceutically acceptable salt or hydrate thereof.

2. A compound of claim 1 wherein n is 1.
3. A compound of claim 2 wherein R is H.
4. The compound of claim 3 that is 1-(3,5-difluorobenzyl)-5-[(4-methyl-1-piperazinyl)methyl]-2-mercaptoimidazole.
5. A pharmaceutical composition for inhibiting dopamine-$\beta$-hydroxylase activity comprising a pharmaceutical carrier and an effective amount of a compound of claim 1.
6. A composition of claim 5 in which the compound is 1-(3,5-difluorobenzyl)-5-[(4-methyl-1-piperazinyl)methyl]-2-mercaptoimidazole.
7. A method of inhibiting dopamine-$\beta$-hydroxylase activity in mammals that comprises administering internally to a subject in need of such inhibition an effective amount of a compound of claim 1.
8. The method of claim 7 in which the compound is 1-(3,5-difluorobenzyl)-5-[(4-methyl-1-piperazinyl)methyl]-2-mercaptoimidazole.
9. A compound represented by the formula:

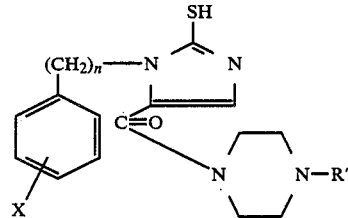

in which:
X is hydrogen, 3,5-difluoro, 2-methoxy, 2-hydroxy, 3-nitro, 3,5-difluoro-4-ethoxy, 3,5-dichloro-2-methyl-4-acetoxy, or 3-trifluoromethyl-5-hydroxymethyl;
R' is H or $C_{1-4}$alkyl; and
n is 1–5.

* * * * *

UNITED STATES PATENT AND TRADEMARK OFFICE
CERTIFICATE OF CORRECTION

PATENT NO. : 4,835,154

DATED : May 30, 1989

INVENTOR(S) : Joseph A. Finkelstein and Lawrence I. Kruse

It is certified that error appears in the above-identified patent and that said Letters Patent is hereby corrected as shown below:

In Claim 1, at column 12, line 12, after "which:" insert --X is--.

Signed and Sealed this

Thirteenth Day of February, 1990

*Attest:*

JEFFREY M. SAMUELS

*Attesting Officer*   *Acting Commissioner of Patents and Trademarks*